(12) United States Patent
Richter-Friis et al.

(10) Patent No.: US 8,551,491 B2
(45) Date of Patent: Oct. 8, 2013

(54) PROCESSES FOR THE PREPARATION OF A BATCH OF AN ACTIVE PHARMACEUTICAL INGREDIENT, A CONTAINER COMPRISING CRYOGRANULES OF AN ALLERGEN PRODUCT, AND A CRYOGRANULE OF AN ALLERGEN PRODUCT

(75) Inventors: Martin Richter-Friis, Fredensborg (DK); Signe Andersen Kolmos, Brenshoj (DK)

(73) Assignee: Alk-Abello A/S, Horsholm (DK)

( * ) Notice: Subject to any disclaimer, the term of this patent is extended or adjusted under 35 U.S.C. 154(b) by 60 days.

(21) Appl. No.: 12/945,814

(22) Filed: Nov. 12, 2010

(65) Prior Publication Data

US 2011/0104216 A1     May 5, 2011

Related U.S. Application Data

(62) Division of application No. 11/014,959, filed on Dec. 20, 2004, now abandoned.

(60) Provisional application No. 60/531,679, filed on Dec. 23, 2003.

(30) Foreign Application Priority Data

Dec. 19, 2003   (DK) .................................. 200301896

(51) Int. Cl.
| | |
|---|---|
| A61K 39/00 | (2006.01) |
| A61K 39/35 | (2006.01) |
| A61K 39/36 | (2006.01) |
| A61K 39/38 | (2006.01) |
| C07K 1/00 | (2006.01) |
| C07K 14/00 | (2006.01) |
| C07K 17/00 | (2006.01) |

(52) U.S. Cl.
USPC ..................... 424/184.1; 424/275.1; 530/350

(58) Field of Classification Search
None
See application file for complete search history.

(56) References Cited

U.S. PATENT DOCUMENTS

| | | | |
|---|---|---|---|
| 4,848,094 A | 7/1989 | Davis et al. | |
| 4,920,923 A | 5/1990 | Hosoya | |
| 5,275,016 A | 1/1994 | Chatterjee et al. | |
| 6,106,836 A | 8/2000 | Wilderbeek et al. | |
| 6,565,888 B1 | 5/2003 | Tracy et al. | |
| 2004/0228919 A1* | 11/2004 | Houghton et al. | 424/484 |
| 2006/0051372 A1* | 3/2006 | Vande Velde | 424/202.1 |

FOREIGN PATENT DOCUMENTS

| | | |
|---|---|---|
| EP | 0621453 | 10/1994 |
| JP | 50-129711 | 10/1975 |
| JP | 2003-519651 | 6/2003 |
| WO | WO-99/47680 A1 | 9/1999 |
| WO | WO-00/06179 | 2/2000 |
| WO | WO-01/51032 | 7/2001 |
| WO | WO-02/40676 A2 | 5/2002 |
| WO | WO 03/020959 | 3/2003 |
| WO | WO-03/096869 A2 | 11/2003 |

OTHER PUBLICATIONS

Schmidt, David J. et al., "Cryogranulation: A potential new final process for bulk drug substances," Nature, Apr. 1997, pp. 28-32.

Malucelli, Maria Ivete Carboni et al., "Evaluation of the polarographic technique for assay of the viability of freeze-dried BCG vaccine: II. Viability of the vaccine assessed by polarography, Warburg respirometry and colony counting," Vaccine, Vo. 13, No. 3, pp. 273-275, 1995.

Patent Abstracts of Japan vol. 014, No. 469 (M-1034) Oct. 12, 1990 & JP 02 187583 A (Yasuto Ozaki) Jul. 23, 1990, abstract.

It's Your Health [online], www.hs-sc.gc.ca [retrieved on Oct. 23, 2008], Retreived from the Internet: <URL: http://www.hc-so.gc.ca/hl-vs/alt_formats/pacrb-dgapcr/pdf/iyh-vsv/med/allergies-eng.pdf.

Schmidt, David J. et al., "Cryogranulation: A Potential New Final Process for Bulk Drug Substances," BioPharm, 1997, vol. 10, No. 4, pp. 28, 30 and 32.

* cited by examiner

*Primary Examiner* — Nora Rooney
(74) *Attorney, Agent, or Firm* — Birch, Stewart, Kolasch & Birch, LLP

(57) ABSTRACT

The present invention relates to processes for the preparation of a batch of an active pharmaceutical ingredient, e.g. an allergen product. The invention also relates to a container comprising cryogranules of a liquid composition of an allergen product, and to a cryogranule of an allergen product. The processes feature formation of cryogranules using a container having therein a cryogenic medium (e.g. liquid nitrogen) and storage of the cryogranules in the same container. The cryogranules obtained can be stored and handled without prior freeze-drying.

4 Claims, 1 Drawing Sheet

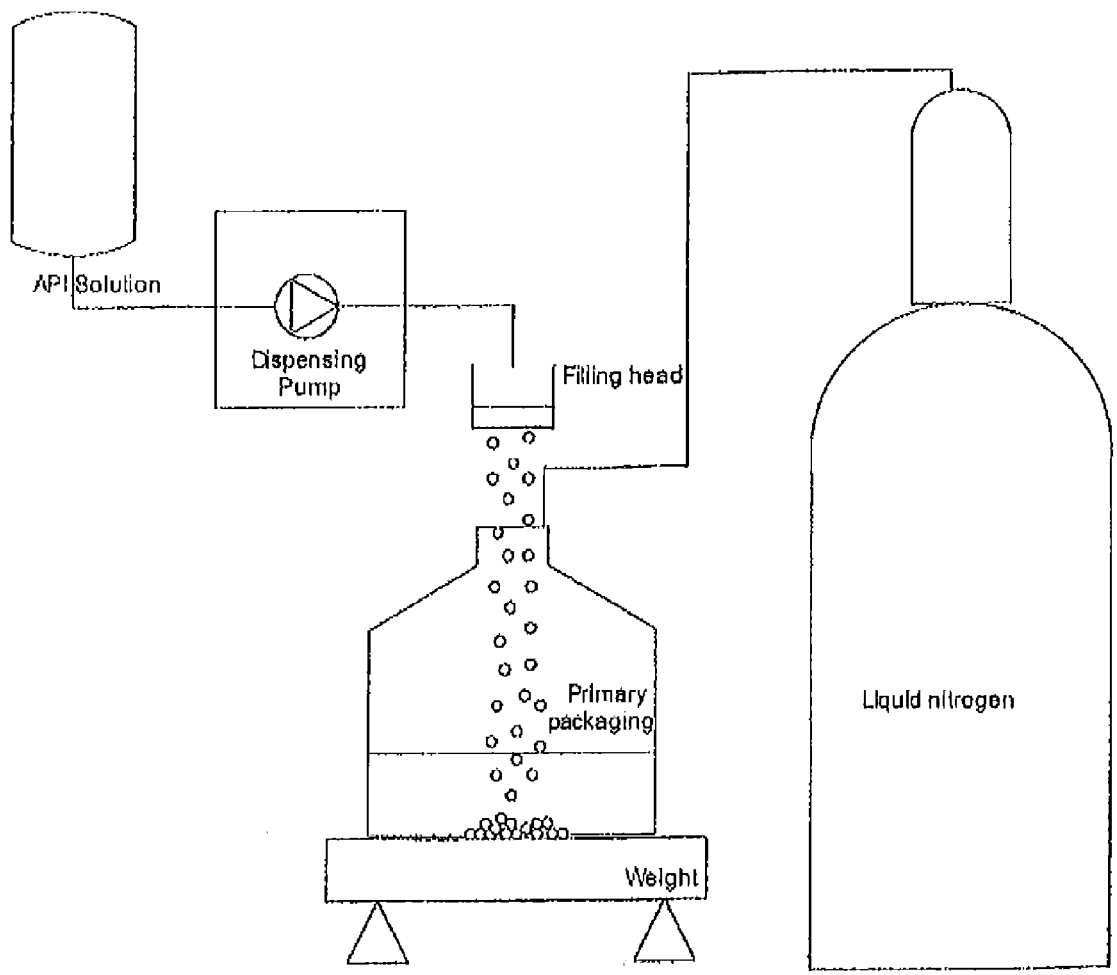

PROCESSES FOR THE PREPARATION OF A BATCH OF AN ACTIVE PHARMACEUTICAL INGREDIENT, A CONTAINER COMPRISING CRYOGRANULES OF AN ALLERGEN PRODUCT, AND A CRYOGRANULE OF AN ALLERGEN PRODUCT

This application is a Divisional of co-pending application Ser. No. 11/014,959 filed on Dec. 20, 2004, and for which priority is claimed under 35 U.S.C. §120; and this application claims priority to Application No. PA 2003-01896 filed in Denmark on Dec. 19, 2003 and U.S. Provisional Application No. 60/531,679 filed on Dec. 23, 2003 under 35 U.S.C. §19; the entire contents of all are hereby incorporated by reference.

FIELD OF THE INVENTION

The present invention relates to processes for the preparation of a batch of an active pharmaceutical ingredient. The invention also relates to a sealed container comprising cryogranules of a liquid composition of an allergen product, and to a cryogranule of an allergen product.

BACKGROUND OF THE INVENTION

Preparation and subsequent formulation of a wide range of active pharmaceutical ingredients, in particular protein-based ingredients, typically define certain requirement with respect to the storage stability, homogeneity and ease of handling of the bulk materials used in such preparations and formulations. Allergen products are examples of such bulk materials. Allergen products are often obtained in an aqueous solution, and such aqueous solutions are most often freeze-dried before storage. However, for industrial scale preparation and formulation, freeze-drying is not particularly suitable due to the fact that (i) it is laborious and work-consuming to freeze-dry large quantities of material, (ii) freeze-drying requires expensive equipment; (iii) reconstitution of the product is often laborious and time-consuming.

WO 00/06179 (Eli Lilly & Co.) discloses a method of processing an aqueous solution of activated protein C (aPC) into a state suitable for storage, handling and recovery. The method comprises the steps of (i) dividing the solution into drops, and (ii) freezing the drops into cryogranules using a stream of liquid nitrogen. The stream of liquid nitrogen and cryogranules are subsequently led to a conveyor that holds back the cryogranules and allows the liquid nitrogen to fall through. The cryogranules can be collected and stored in a sealed container. The cryogranules can afterwards be used as starting material for commercial scale production of a pharmaceutical composition. The preparation of the cryogranules, however, requires complicated equipment, e.g. a cryogranulation unit including the before-mentioned conveyor that is difficult to maintain and clean. Furthermore, implementation of GMP protocols for using a cryogranulation unit is laborious and time-consuming.

WO 03/20959 (BTF Pty Ltd) discloses a method for the preparation of products containing a quantum of bioparticles, wherein the method i.a. comprises the steps of forming a solid body by placing a droplet in a container that comprises a cryogenic liquid so as to form a frozen body, subsequently drying (e.g. freeze-drying) the frozen body to form a substantially dry solid product within the container, and, if desired, capping or sealing the container for storage and transport of the product.

In spite of the above, there is still a need for a more rational process for industrial scale preparation of batches of active pharmaceutical ingredients that are suitable for handling and storage.

BRIEF DESCRIPTION OF THE INVENTION

The present invention provides rationalized processes for industrial scale preparation of batches of active pharmaceutical ingredients that are suitable for handling and storage.

A first aspect of the present invention relates to the process defined in claim 1.

A second aspect of the present invention relates to the process defined in claim 2.

A third aspect of the present invention relates to the process defined in claim 3.

The invention further provides a container comprising cryogranules of a liquid composition of an allergen product.

Still further, the present invention provides a cryogranule of a liquid composition of an allergen product.

The invention thus provides efficient processes that overcome the problems of the prior art in that the process does not require complicated cryogranulation equipment or tedious freeze-drying steps. Furthermore, the process of the present invention renders it possible to prepare sterile cryogranules.

BRIEF DESCRIPTION OF THE DRAWINGS

FIG. 1 illustrates a simple arrangement useful for the method of the present invention. Liquid nitrogen is initially loaded into a suitable container (e.g. a primary packaging). After loading of the liquid nitrogen, the active pharmaceutical ingredient is pumped from a reservoir to a filling head by means of a dispensing pump, e.g. a peristaltic pump. Droplets are formed from apertures in the lower part of the filling head, and the droplets leave the filling head and fall into the cryogenic medium (nitrogen) in the container whereby cryogranules are formed. The container may be placed on a weight for the purpose of following the evaporation of liquid nitrogen and formation of cryogranules of the active pharmaceutical ingredient.

DETAILED DESCRIPTION OF THE INVENTION

As mentioned above, the present invention provides processes for the preparation of a batch of an active pharmaceutical ingredient.

Step (a)—Liquid Composition

The processes comprise a first step of (a) providing a liquid composition comprising the active pharmaceutical ingredient, where the liquid composition has a freezing temperature.

The liquid composition is preferably an aqueous solution or suspension, in particular an aqueous solution. Aqueous solutions are typically liquid solutions comprising at least 50% (v/v) water. Examples hereof are pure water and water in combination with one or more miscible solvents such as short-chain alcohols, e.g. methanol, ethanol, n-propanol and isopropanol, short-chain ketones, e.g. acetone, and polyalcohols, e.g. glycerol. The liquid composition (e.g. the aqueous solution) may further comprise pharmaceutically acceptable solutes such as sugars, e.g. sucrose, and detergents, e.g. non-ionic surfactants.

Active pharmaceutical ingredients for which the present invention is particularly applicable are those that are susceptible to degradation by shear forces, e.g. repeated freeze-thaw cycles. Particular examples here of are allergen products and protein-based ingredients, e.g. enzyme preparation, etc. The currently most interesting active pharmaceutical ingredient is an allergen product.

In the present description and claims, the term "allergen product" is intended to mean a product useful in the treatment, alleviation or prophylaxis of allergenic reactions in humans or animals. Particularly relevant "allergen products" comprise a naturally occurring protein that has been reported to induce allergic, i.e. IgE mediated reactions, upon its repeated exposure to an individual. Examples of naturally occurring allergens include pollen allergens (tree-, herb, weed-, and grass pollen allergens), insect allergens (inhalant, saliva and venom allergens, e.g. mite allergens, cockroach and midges allergens, hymenopthera venom allergens), animal hair and dandruff allergens (from e.g. dog, cat, horse, rat, mouse etc.), and food allergens. Important pollen allergens from trees, grasses and herbs are such originating from the taxonomic orders of Fagales, Oleales, finales and platanaceae including i.a. birch (Betula), alder (Alnus), hazel (Corylus), hornbeam (Carpinus) and olive (Olea), cedar (Cryptomeria and Juniperus), Plane tree (Platanus), the order of Poales including i.a. grasses of the genera *Lolium, Phleum, Poa, Cynodon, Dactylis, Holcus, Phalaris, Secale,* and *Sorghum,* the orders of Asterales and Urticales including i.a. herbs of the genera *Ambrosia, Artemisia,* and *Parietaria.* Other important inhalation allergens are those from house dust mites of the genus *Dermatophagoides* and *Euroglyphus,* storage mite e.g *Lepidoglyphys, Glycyphagus* and *Tyrophagus,* those from cockroaches, midges and fleas e.g. *Blatella, Periplaneta, Chironomus* and *Ctenocepphalides,* and those from mammals such as cat, dog and horse, venom allergens including such originating from stinging or biting insects such as those from the taxonomic order of Hymenoptera including bees (superfamily Apidae), wasps (superfamily Vespidea), and ants (superfamily Formicoidae). Important inhalation allergens from fungi are i.a. such originating from the genera *Alternaria* and *Cladosporium.*

In some preferred embodiments of the invention, the allergen is selected from Bet v 1, Aln g 1, Cor a 1 and Car b 1, Que a 1, Cry j 1, Cry j 2, Cup a 1, Cup s 1, Jun a 1, Jun a 2, jun a 3, Ole e 1, Lig v 1, Pla l 1, Pla a 2, Amb a 1, Amb a 2, Amb t 5, Art v 1, Art v 2, Par j 1, Par j 2, Par j 3, Sal k 1, Ave e 1, Cyn d 1, Cyn d 7, Dac g 1, Fes p 1, Hol l 1, Lol p 1 and 5, Pha a 1, Pas n 1, Phl p 1, Phl p 5, Phl p 6, Poa p 1, Poa p 5, Sec c 1, Sec c 5, Sor h 1, Der f 1, Der f 2, Der p 1, Der p 2, Der p 7, Der m 1, Eur m 2, Gly d 1, Lep d 2, Blo t 1, Tyr p 2, Bla g 1, Bla g 2, Per a 1, Fel d 1, Can f 1, Can f 2, Bos d 2, Equ c 1, Equ c 2, Equ c 3, Mus m 1, Rat n 1, Apis m 1, Api m 2, Ves v 1, Ves v 2, Ves v 5, Dol m 1, Dil m 2, Dol m 5, Pol a 1, Pol a 2, Pol a 5, Sol i 1, Sol i 2, Sol i 3 and Sol i 4, Alt a 1, Cla h 1, Asp f 1, Bos d 4, Mal d 1, Gly m 1, Gly m 2, Gly m 3, Ara h 1, Ara h 2, Ara b 3, Ara h 4, Ara h 5 and shufflant hybrids from molecular breeding of any of these.

In the most preferred embodiment of the invention, the allergen is a grass pollen allergen or a dust mite allergen or a ragweed allergen or a cedar pollen or a cat allergen or birch allergen.

In yet another embodiment of the invention, the allergen product comprises at least two different types of allergens either originating from the same allergic source or originating from different allergenic sources e.g. grass group 1 and grass group 5 allergens or mite group 1 and group 2 allergens from different mite and grass species respectively, weed antigens like short and giant ragweed allergens, different fungi allergens like *Alternaria* and *Cladosporium,* tree allergens like birch, hazel, hornbeam, oak and alder allergens, food allergens like peanut, soybean and milk allergens.

The allergen product may be in the form of an extract, a purified allergen, a modified allergen, a recombinant allergen or a mutant of a recombinant allergen. An allergenic extract may naturally contain one or more isoforms of the same allergen, whereas a recombinant allergen typically only represents one isoform of an allergen. In a preferred embodiment, the allergen is in the form of an extract. In another preferred embodiment, the allergen is a recombinant allergen. In a further preferred embodiment, the allergen is a naturally occurring low IgE-binding mutant or a recombinant low IgE-binding mutant.

When the allergen product contains two or more allergens, the allergens may be present in equimolar amounts or the molar ratio of the allergens present may vary, preferably from 20:1 to 1:20.

In a particular embodiment of the invention, the low IgE binding allergen is an allergen according to WO 99/47680, WO 02/40676 or WO 03/096869 A2.

The concentration of the active pharmaceutical ingredient in the liquid composition is typically in the range of 1-500 mg/mL, e.g. in the range of 1-300 mg/mL, such as in the range of 5-100 mg/mL, e.g. around 20-80 mg/mL.

Typically, the liquid composition should have a freezing temperature of at least $-30°$ C., e.g. at least $-10°$ C., so that droplets of the composition freeze rapidly when getting in contact with the cryogenic medium. Aqueous solutions typically have a freezing temperature in the range of from $-10°$ C. to $0°$ C.

In some particular embodiments, the liquid composition is sterile, and the processes are then preferably conducted under sterile conditions.

Step (b)—Container and Cryogenic Medium

The processes further comprise the step of (b) providing a container comprising therein a cryogenic medium having a boiling temperature below the freezing temperature of the liquid composition.

The container to be used in conjunction with the invention should typically be able to withstand temperature variations from $-200°$ C. to $+120°$ C. corresponding, on the one hand, to the boiling temperature for liquid nitrogen at atmospheric pressure and, on the other hand, to a typical temperature used for sterilization of equipment. Thus, the container is typically made of a metal or alloy, a ceramic material, glass, a plastic or a cardboard material, in particular of a metal or alloy such as aluminium or stainless steel, or of glass or a ceramic material.

In one embodiment, the container is a cylindrical container, e.g. a cylindrical aluminium container. Cylindrical or rounded containers have the advantage that, due to the absence of edges and corners, they will be easy to clean after use.

As an alternative, the container may have the form of a tray such that a larger number of droplets can be added simultaneously to the container.

For industrial size processes, the volume of the container is typically at least 1 L, e.g. 5 L or more, such as 20 L or more, and even 60 L or more. It is a particular feature of the process of the invention that it is applicable for industrial scale batches. The load of the cryogranules of the liquid composition in each container may, e.g., be 30 kg for a 60 L container.

A feature of the invention is also to provide a batch of cryogranules of a composition comprising the active pharmaceutical ingredient directly in a container suitable for storing and handling. Thus, the sealable container should typically have a sufficient cross-section of the opening so that the liquid composition in the form of droplets can be added to the cryogenic medium contained in the container at a reasonable rate. The cross-sectional area of the opening is preferably 5-100% of the inner cross-sectional area of the container so that the droplets can be added simultaneously to a substantial area of the surface of the cryogenic medium.

The container in which the cryogranules are formed is preferably sealed after addition of the liquid composition to the cryogenic medium, however, most often after at least partial removal of the cryogenic medium. Thus, in a preferred embodiment of the processes of the invention, the container is sealed by means of a sealing means.

The sealing means for the container may have the form of a cap, a screw cap, a plug, a lid, a foil (e.g. a plastic or metal foil), etc. The person skilled in the art will, of course, be able to select a suitable sealing means in order to ensure that moisture, dirt, and air is effectively prohibited from entering the container after sealing thereof. Furthermore, the sealing means should preferably also ensure that the active pharmaceutical ingredient is not allowed to sublimate to the exterior of the container. In one embodiment, the sealing means is a cap comprising a butyl rubber disc or plug. The container should, where applicable, comprise a flange or lip corresponding to the chosen type of sealing means.

Sealing of a container in the form of a tray can, e.g., be effected by covering the tray with a lid, wrapping the tray in a plastic or metal foil, or placing the tray in a bag of a plastic or metal foil.

In one embodiment, the sealing means or the container wall comprises a one-way valve for allowing excess pressure in the sealed container to escape. In one embodiment, the one-way valve is arranged in the wall of the container; in another embodiment, the one-way valve is arranged in the sealing means; and in still another embodiment, the one-way valve function is obtained in the way the sealing means interacts with the container opening. Incorporation of a one-way valve is particularly relevant in the event where the container is sealed before the entire cryogenic medium has been allowed to escape from the container. Also, the one-way valve eliminates the risk of explosion or breakage of the seal, should the pressure in the container unexpectedly increase. The one-way valve preferably allows an excess pressure below a certain threshold (e.g. an excess pressure of up to 100 kPa or up to 50 kPa relative to the ambient pressure) to exist in the container so that air and moisture are further prevented from entering the sealed container.

The cryogenic medium should preferably have a boiling temperature of at the most −40° C., such as at the most −75° C., and preferably at the most −150° C. The cryogenic medium is typically selected from liquid nitrogen, liquid helium and liquid oxygen, preferably liquid nitrogen.

The container is typically loaded to an extent of 10-100%, e.g. 50-95%, such as 60-90%, with the cryogenic medium, e.g. liquid nitrogen.

In order to maintain a suitably low temperature in the container, the container may be insulated or may have a double wall, e.g. vacuum chamber. Insulation may also be effected by a mantle of an insulating material, e.g. foamed polystyrene (Flamingo).

Step (c)—Formation of Cryogranules

The process further comprises the step of (c) dividing the liquid composition into droplets, and adding said droplets to the cryogenic medium in the container whereby said droplets freeze to form cryogranules of the liquid composition.

The liquid composition is typically divided into droplets by means of a filling head comprising one or more apertures (e.g. nozzles or needles), preferably a plurality of apertures. The opening of each aperture is typically so that the average diameter of the droplets (and thereby also the cryogranules) will be in the range of 0.1-20 mm, such as 0.5-10 mm, e.g. 1-5 mm.

The shape of the cryogranules formed in the process of the invention depends on the process conditions, and the shape of the cryogranules ranges from being approximately spherical in shape to being fairly irregular in shape. In connection with the present invention, the expression "diameter" in connection with cryogranules means the largest dimension of the cryogranule.

The amount of liquid composition required for each droplet is typically in the range of 0.5-250 µL, e.g. 1-100 µL such as 2-20 µL. Although it is not particularly critical, uniformity of the cryogranules is normally desirable, and the flow rate to the aperture(s) should preferably be adjusted so that excessive aggregation of droplets at the surface of the cryogenic medium is suppressed. A typical flow rate is 0.060-25 mL/min per aperture. The liquid composition is typically fed to each aperture such that 1-4, e.g. 1-2, drops are formed per second.

It is also envisaged that droplet-formation technologies usually known from the inkjet printers may be useful for the formation of droplets of the liquid composition.

The viscosity and/or surface tension of the droplets may optionally be adjusted by proper selection of the solvent and addition of pharmaceutically acceptable solutes such as sugars and non-ionic surfactants.

The droplets are added directly to the cryogenic medium after leaving the aperture(s) and will normally freeze fairly rapidly to form cryogranules of the liquid composition.

The expression "cryogranules" is intended to mean frozen granules of the liquid composition obtained after contact with the cryogenic medium (e.g. liquid nitrogen). It should be understood that "cryogranules" may be formed by two or more droplets due to the fact that some of the already frozen droplets (cryogranules) tend to float on the surface of the cryogenic medium whereby subsequently added droplets tend to hit and thereby aggregate with such initially formed cryogranules. Thus, in some embodiment, it should be understood that a cryogranule may be formed from 2-50 aggregated droplets, more typically 2-20 aggregated droplets.

This being said, a batch of cryogranules will in many instances be a mixture of cryogranules corresponding to one frozen droplet and cryogranules corresponding to aggregates of two or more frozen droplets. Accordingly, the (number) "average diameter" of the cryogranules refers to such a batch (mixture) of cryogranules.

For the purpose of the subsequent handling of the cryogranules, it is often preferred that less than 1% of the cryogranules are aggregates of more than 25 droplets.

The filling head and nozzles from which the droplets are formed are typically arranged just above the opening of the container, within the opening path, or within the container.

In one embodiment, the filling head holds a sufficient number of apertures so that the droplets are distributed over a cross-sectional area corresponding to slightly less (e.g. 90%) than the cross-sectional area of the opening of the container.

In an alternative embodiment, e.g. applicable for cylindrical containers, in particular where the cross-sectional area of the opening of the container is less than 80%, or even less than 60%, of the cross-sectional area of the container, the filling head may be constructed so that it can be arranged within the container and thereby cover a cross-sectional area larger than the cross-sectional area of the opening of the container. This embodiment can be materialized by using a filling head in the form of a rotating bar having laterally arranged apertures. The bar can then be placed in the container just above the level of the cryogenic medium, and feeding and rotation of the bar will render distribution of the droplets over substantially the entire cross-sectional area possible.

In both embodiments, it is preferred that the filling head is arranged in such a way that freezing of a droplet does not occur before the individual droplet has left the respective aperture.

General considerations with respect to the preparation of cryogranules can be found in U.S. Pat. No. 5,275,016, U.S. Pat. No. 4,848,094, WO 00/06179 and WO 03/020959.

Step (d)—Storage

A common feature of the processes of the present invention is that the cryogranules are stored as such, e.g. without any drying (e.g. freeze-drying) thereof. A convenient feature of the invention is also that the cryogranules can be stored in the same container as the one used in connection with the formation of the cryogranules.

Thus, according to the first aspect of the invention, a final step of the process comprises sealing of the container containing the cryogranules of the liquid composition with the sealing means, and storing the container. Sealing is, of course, typically effected by means of the selected sealing means.

According to the second aspect of the invention, a final step of the process comprises storing the container containing the cryogranules of the liquid composition for a period of not less than 24 hours. More typically the container is stored for a period of not less than 48 hours, such as not less than 96 hours, e.g. for 1 or even 4 weeks.

According to the third aspect of the invention, a final step of the process comprises storing the container containing the cryogranules of the liquid composition; with the proviso that the cryogranules of the liquid composition are not subjected to a freeze-drying step subsequent to step (c) or step (d).

In all instances, the sealed container is preferably subsequently stored at a temperature below the critical conductivity temperature of the liquid composition so as to avoid clotting or aggregation of the cryogranules that may render it difficult to handle the cryogranules.

The "critical conductivity temperature" is determined as the temperature at which the rate of change, i.e. the first derivative, of the electrical conductivity is significant. The practical way of determining the critical conductivity temperature is to (a) scan the electrical conductivity over a broad temperature range to produce a plot of the electrical conductivity vs. the temperature, (b) calculate the first derivative of the electrical conductivity, and (c) determine the critical conductivity temperature as the temperature where the rate of change (first derivative) of the electrical conductivity is significant.

In most embodiments, the container (sealed or not) is preferably stored at a temperature of in the range of from $-80°$ C. to $0°$ C., such as from $-40°$ C. to $-10°$ C. The storing time (which may include handling such as transportation of the container) is typically a period of not less than 24 hours. In many instances, the container is stored for a period of not less than 48 hours, such as not less than 96 hours, e.g. for 1 or even 4 weeks, before the cryogranules are processed further. Preferably, the container containing the cryogranules of the liquid composition is capable of being stored in a period of more than six months, preferably more than one year, preferably more than five years, without loss of the activity of the active pharmaceutical ingredient.

In all aspects of the invention, it is preferred that the container is sealed with a sealing means prior to storage. Sealing ensures that moisture, dirt, and air are effectively prohibited from entering the container.

In one important embodiment thereof, the process comprises the additional step of removing substantially the entire cryogenic medium from the container prior to sealing the container. Removal of the cryogenic medium can be effected by evaporation of the cryogenic medium, by decantation of the cryogenic medium, or by a combination of the two. Removal of the cryogenic medium is particularly relevant in order to avoid the development of hazardous excess pressure in the container after sealing. In order to avoid further clotting or aggregation of the cryogranules, the temperature of the cryogranules is preferably held below the critical conductivity temperature of the liquid composition while the cryogenic medium is removed.

In the alternative embodiment in which at least a portion of the cryogenic medium is still present in the container upon sealing, it is particularly desirable to include the one-way valve in either the sealing means or in the container wall. This embodiment has the advantage that the container is sealed while the container is completely occupied by the cryogenic medium, the cryogranules and the gas corresponding to the cryogenic medium (e.g. nitrogen gas), whereby air and moisture will be excluded from the container. Furthermore, an advantage particularly relevant for industrial scale production may be that the container can be sealed immediately after addition of the droplets whereby costly waiting time before the container can be handled is eliminated.

In one particular embodiment of the present invention, the process comprises the steps of:

(a) providing a liquid composition comprising an allergen product, said liquid composition having a freezing temperature of at least $-30°$ C.;

(b) providing a container and a sealing means suitable for sealing said container, said container comprising therein liquid nitrogen;

(c) dividing the liquid composition into droplets, and adding said droplets to the cryogenic medium in the container whereby said droplets freeze to form cryogranules of the liquid composition, said cryogranules having an average diameter of in the range of 0.5-10 mm; and (d) removing substantially the entire cryogenic medium while the temperature of the cryogranules is held below the critical conductivity temperature of the liquid composition; and sealing said container containing the cryogranules of the liquid composition. In a particular variant of this embodiment, the sealing means or the container wall comprises a one-way valve for allowing excess pressure in the sealed container to escape.

In another particular embodiment of the present invention, the process comprises the steps of:

(a) providing a liquid composition comprising an allergen product, said liquid composition having a freezing temperature of at least $-30°$ C.;

(b) providing a container comprising therein liquid nitrogen;

(c) dividing the liquid composition into droplets, and adding said droplets to the cryogenic medium in the container whereby said droplets freeze to form cryogranules of the liquid composition, said cryogranules having an average diameter of in the range of 0.5-10 mm; and (d) removing substantially the entire cryogenic medium while the temperature of the cryogranules is held below the critical conductivity temperature of the liquid composition; and storing said container containing the cryogranules of the liquid composition for a period of not less than 48 hours.

In a further particular embodiment of the present invention, the process comprises the steps of:

(a) providing a liquid composition comprising an allergen product, said liquid composition having a freezing temperature of at least −30° C.;

(b) providing a container comprising therein liquid nitrogen;

(c) dividing the liquid composition into droplets, and adding said droplets to the cryogenic medium in the container whereby said droplets freeze to form cryogranules of the liquid composition, said cryogranules having an average diameter of in the range of 0.5-10 mm; and (d) removing substantially the entire cryogenic medium while the temperature of the cryogranules is held below the critical conductivity temperature of the liquid composition; and storing said container containing the cryogranules of the liquid composition;

with the proviso that the cryogranules of the liquid composition are not subjected to a freeze-drying step subsequent to step (c) or step (d).

In an even more particular embodiment of the present invention, the process comprises the steps of:

(a) providing a liquid composition comprising an allergen product, said liquid composition having a freezing temperature of at least −30° C.;

(b) providing a container and sealing means suitable for sealing said container, said container comprising therein liquid nitrogen;

(c) dividing the liquid composition into droplets, and adding said droplets to the cryogenic medium in the container whereby said droplets freeze to form cryogranules of the liquid composition, said cryogranules having an average diameter of in the range of 0.5-10 mm; and (d) removing substantially the entire cryogenic medium while the temperature of the cryogranules is held below the critical conductivity temperature of the liquid composition; sealing said container containing the cryogranules of the liquid composition; and storing said sealed container containing the cryogranules of the liquid composition;

with the proviso that the cryogranules of the liquid composition are not subjected to a freeze-drying step subsequent to step (c) or step (d). In a particular variant of this embodiment, the sealing means or the container wall comprises a one-way valve for allowing excess pressure in the sealed container to escape.

Following the above, the present invention also provides a container, in particular a sealed container (i.e. sealed by a sealing means), comprising cryogranules of a liquid composition of an allergen product, said cryogranules having an average diameter of in the range of 0.1-20 mm, such as in the range of 0.5-10 mm. In one embodiment, the sealing means or the container wall comprises a one-way valve for allowing excess pressure in the sealed container to escape. The container preferably has some of the characteristics defined above in connection with the description of the processes of the invention. In one embodiment, the container is obtainable by a process defined herein.

Still further, the present invention also provides a cryogranule of a liquid composition of an allergen product, said cryogranule having an average diameter of in the range of 0.1-20 mm, such as in the range of 0.5-10 mm. The cryogranule preferably has some of the characteristics defined above in connection with the description of the processes of the invention. In one embodiment, the cryogranule is prepared essentially as defined herein.

The cryogranules are typically used directly in suitable formulation processes. As a result of the processes defined herein, individual aliquots of the batch of cryogranules exhibit a high degree of homogeneity, thus the batch of the cryogranules can easily be standardized for further use in formulation processes.

EXAMPLES

Preparation of Cryogranules of an Allergen Product 700 mL of a liquid composition of an allergen product was produced by extraction of *Phleum pratense* grass pollen source material, according to the methodology described in "Allergenic extracts", H. Ipsen et al, chapter 20 in Allergy, principle and practise (Ed. S. Manning) 1993, Mosby-Year Book, St. Louis. The liquid composition comprised about 50 mg of the allergen product per mL.

The arrangement illustrated in FIG. 1 was used for the formation of cryogranules. The liquid composition was held in a single-use Flexboy bag (STEDIM, France). The bag was connected to a dispensing pump (Fill-Master power unit type 042, Control unit type 401, Pump unit type 403, and Pump head type 112, all from Delta Scientific Medical) by means of a suitable Masterflex tubing (Rehau). A Masterflex tubing connected to the dispensing pump ended just above a filling head (a custom-made stainless steel cup (Ø107 mm) with 5 apertures (Ø1 mm) with downwardly pointing protrusions for uniform drop formation). The filling head was arranged 15 cm above the opening of a Pharma 802, 5.5 L aluminium container (Tournaire, France). The container was placed on a QS32A weight (Sartorius) for monitoring the evaporation of nitrogen and formation of the cryogranules. The container was initially 90% filled with liquid nitrogen from a stainless steel tank.

The liquid composition was added to the filling head at a rate of approximately 50 ml/min over a period of about 14 min. The open container was held at about 20° C. for 2 hours whereby liquid nitrogen evaporated off. Initially, the container was sealed with a bytyl rubber plug and a seal lever ring so as to allow removal of the plug for sample withdrawing. Subsequently, the butyl rubber plug was sealed with a metal cap, and the container was stored at −20° C. before the cryogranules containing the allergen product were weighed out and formulated in suitable doses (storage time typically 6 to 12 months). The cryogranules were not freeze-dried before formulation.

The invention claimed is:

1. A storage stable composition consisting of non-freeze dried frozen granules of an aqueous composition of a naturally occurring pollen allergen or mite allergen, wherein said non-freeze dried frozen granules have an average diameter in the range of 0.5-10 mm and wherein the composition can be stored for more than 1 year at a temperature in the range of −40° C. to −10° C. without loss of the allergen activity and wherein the composition is intended for being weighed out and formulated into suitable doses.

2. The composition according to claim 1, wherein said non-freeze dried frozen granules have an average diameter of in the range of 1-5 mm.

3. A container comprising the composition of claim 1.

4. The composition according to claim 1, wherein the pollen allergen is a tree, herb, weed or grass pollen allergen.

* * * * *